(12) United States Patent
O'Hara et al.

(10) Patent No.: US 8,956,635 B2
(45) Date of Patent: Feb. 17, 2015

(54) INSECT REPELLENT DEVICES

(75) Inventors: John O'Hara, Riverside, CA (US); J. Monte Ross, Monrovia, CA (US)

(73) Assignee: Fly Armor, LLC., Lexington, SC (US)

( * ) Notice: Subject to any disclaimer, the term of this patent is extended or adjusted under 35 U.S.C. 154(b) by 0 days.

(21) Appl. No.: 13/477,502

(22) Filed: May 22, 2012

(65) Prior Publication Data

US 2012/0315317 A1 Dec. 13, 2012

Related U.S. Application Data

(60) Provisional application No. 61/494,359, filed on Jun. 7, 2011.

(51) Int. Cl.
| | | |
|---|---|---|
| *A01N 25/00* | (2006.01) | |
| *A01N 25/08* | (2006.01) | |
| *A01N 25/34* | (2006.01) | |
| *A01N 65/44* | (2009.01) | |

(52) U.S. Cl.
CPC ............... *A01N 25/08* (2013.01); *A01N 25/34* (2013.01); *A01N 65/44* (2013.01)
USPC ...................................................... 424/405

(58) Field of Classification Search
None
See application file for complete search history.

(56) References Cited

U.S. PATENT DOCUMENTS

| | | |
|---|---|---|
| 173,945 A | 2/1876 | Swan et al. |
| 233,954 A | 11/1880 | Thompson |
| 2,219,569 A | 8/1938 | Vanderhoof |
| 2,342,066 A | 2/1944 | Tramill |
| 2,401,253 A | 5/1946 | Lamb, Jr. |
| 2,734,483 A | 2/1956 | Peo |
| 2,791,202 A | 5/1957 | Doyle |
| 3,811,413 A | 5/1974 | Scherpenborg |
| 3,814,061 A | 6/1974 | Aries et al. |
| 3,978,820 A | 9/1976 | Drehman |
| 4,068,624 A | 1/1978 | Ramney |
| 4,145,001 A | 3/1979 | Weyenberg et al. |
| 4,184,452 A | 1/1980 | Buzzell et al. |
| 4,218,991 A | 8/1980 | Cole |
| 4,224,901 A | 9/1980 | Carey, Jr. |
| 4,506,630 A | 3/1985 | Hair |
| 4,662,156 A | 5/1987 | Oettel |
| 4,671,960 A | 6/1987 | Thielen et al. |
| 4,876,090 A | 10/1989 | Weisler |
| 4,900,876 A | 2/1990 | Bushman et al. |
| 5,003,756 A | 4/1991 | Mazzotta, Sr. |
| 5,109,803 A | 5/1992 | Dunham et al. |
| 5,184,573 A | 2/1993 | Stevens, Jr. |
| 5,341,627 A | 8/1994 | Eby |
| 5,555,848 A | 9/1996 | Trujillo |
| 5,735,460 A * | 4/1998 | Eisenbraun ..................... 239/34 |
| 5,970,921 A | 10/1999 | Fulton |
| 6,101,981 A | 8/2000 | Friend et al. |
| 6,234,118 B1 | 5/2001 | Lahens |
| 6,251,431 B1 * | 6/2001 | Van Rees ...................... 424/469 |
| 6,382,137 B1 | 5/2002 | Derrieu et al. |
| 7,185,613 B2 | 3/2007 | Arvanitis |
| 7,427,417 B2 | 9/2008 | Jendrucko |
| D605,276 S | 12/2009 | Beardmore |
| 7,780,972 B2 | 8/2010 | Hurwitz |
| D630,387 S | 1/2011 | Mendez |
| 2003/0017129 A1 * | 1/2003 | Maleeny et al. ............. 424/76.2 |
| 2005/0019269 A1 | 1/2005 | Marks et al. |
| 2008/0193387 A1 * | 8/2008 | De Wolff ........................ 424/47 |
| 2008/0245315 A1 | 10/2008 | Tyler |

OTHER PUBLICATIONS

Winning Deals, Easy to Wear Mosquito Repellent, web pages, downloaded Sep. 22, 2011, www.windeals.co.uk/mosquito.
Herb Healer Academy Inc., Natural Pet & Livestock Products, web pages, downloaded Aug. 19, 2011, www.herbhealer.com/pets/.
R&R Group, LLC., Defy the Fly, www.defythefly.com, Granite Bay, Ca. (website pages not enclosed), 2014.
An article of manufacture branded "Fly Free Zone" (article not enclosed), 2014.
Judy's Health Cafe, Natural Flea and Tick Control for Dogs and Cats, web pages, downloaded Aug. 19, 2011, www.judyshealthcafe.com/flea-free.html.

* cited by examiner

*Primary Examiner* — Adam C Milligan
(74) *Attorney, Agent, or Firm* — IP and Business Law Offices of Howard L. Hoffenberg, Esq.; Howard Leslie Hoffenberg

(57) ABSTRACT

An insect repellent device that is wearable by a host or attachable to an object, such device comprised of: an elongated band having length and width comprised of an outer surface to face toward a host or object, an inner surface to face away from a host or object, a first end, a second end and at least one impervious region; at least one front panel having a plurality of apertures positioned over the second side opposite an impervious region and that is attached to the elongated band so as to form a vented pocket with an opening; an absorbent pad impregnated with natural oils that is slidably and removably insertable into the vented pocket; and, at least one means for securing connected to an end that provides the user with the ability to replace its absorbent impregnated pads instead of having to buy another new band.

27 Claims, 11 Drawing Sheets

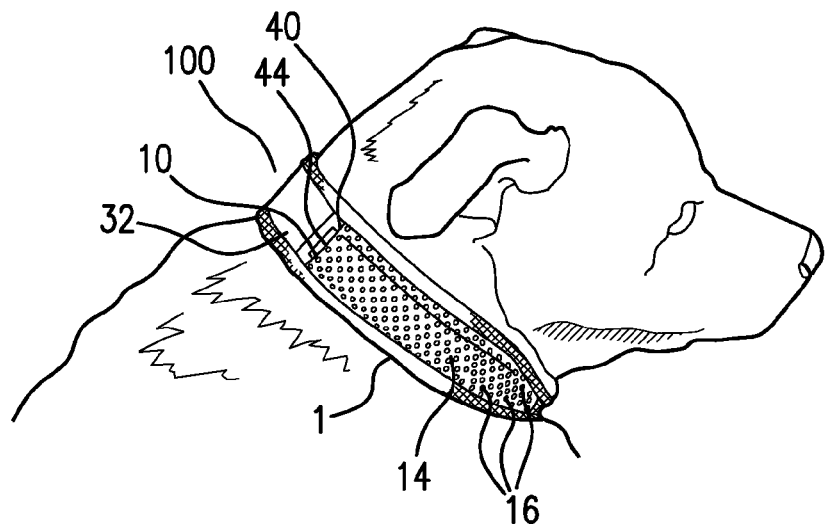
FIG. 3
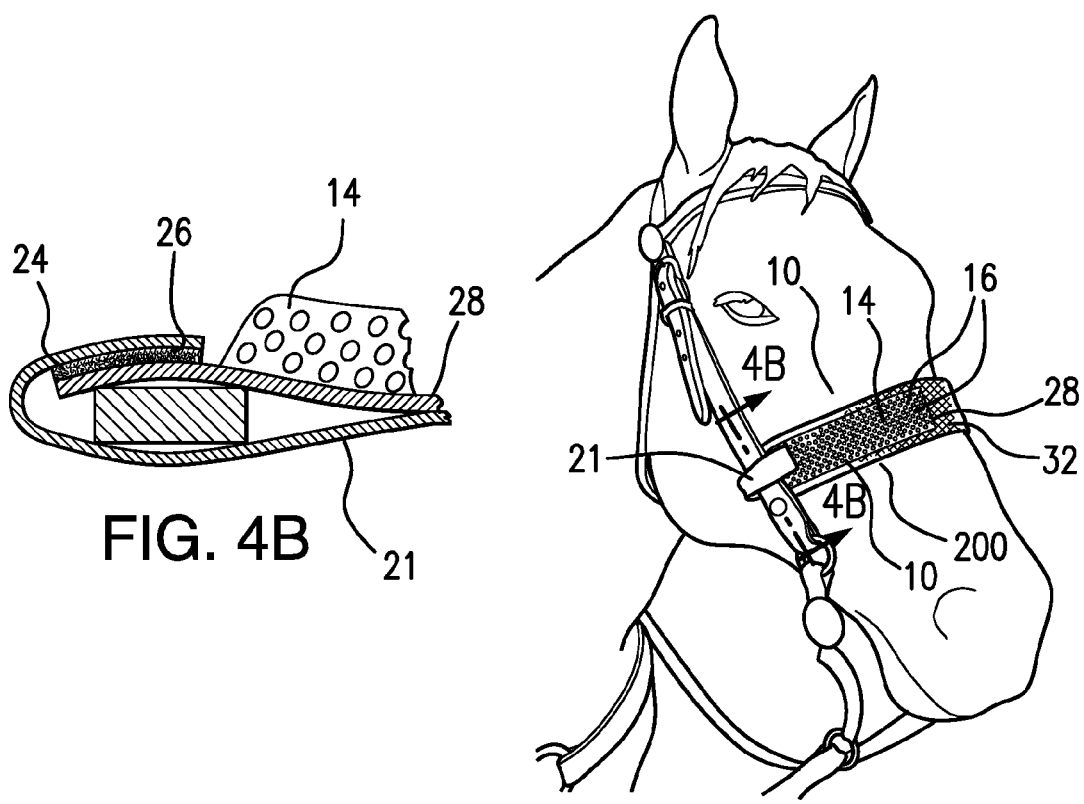
FIG. 4B
FIG. 4A

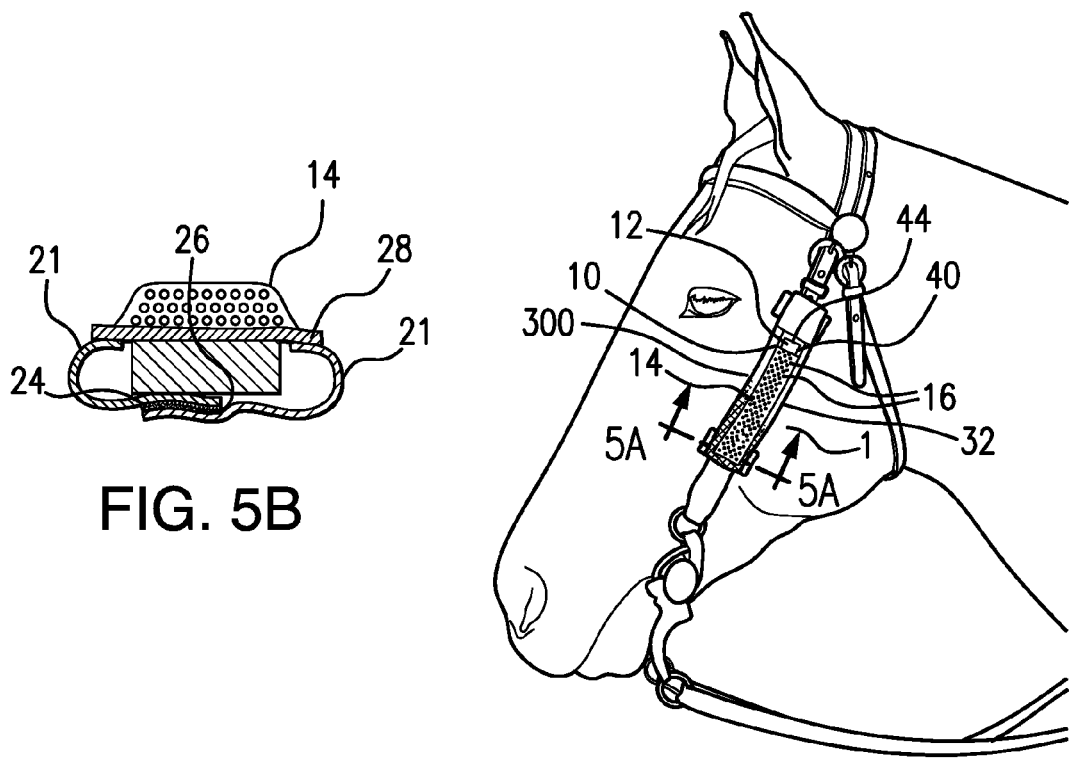
FIG. 5B
FIG. 5A
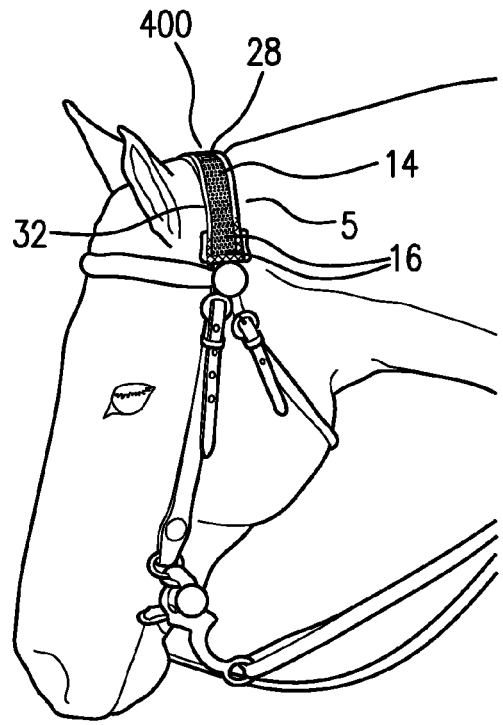
FIG. 6

INSECT REPELLENT DEVICES

PRIORITY CLAIM

This application claims priority to and the benefit of U.S. provisional application Ser. No. 61/494,359 filed on Jun. 7, 2011, the contents of which is incorporated by reference.

BACKGROUND OF THE INVENTION

1. Field of the Invention

This invention pertains generally to insect control devices and more particularly to insect repellent devices.

2. Related Art

A horse is a four legged mammal. It has a head that is comprised of a forehead, muzzle, mouth, eyes, nostrils and ears. The mouth, eyes, nostrils and ears have wet mucosal-like surfaces. A horse engages in anaerobic respiration with exhalation of carbon dioxide.

There is a time-honored place in human existence for horses. Up to the early twentieth century, they were the primary means for transportation and hauling. The racing of horses for exhibition rooted itself in human culture going back at least as far as the Romans and continues today as vibrant exhibition sport. Today, horses are ridden for recreation, racing and utilitarian purposes of transportation and hauling.

Similar to horses, other mammals, such as cows, dogs and humans, have a head that is comprised of a mouth, eyes, nostrils and ears with wet mucosal-like surfaces. These mammals also breathe with exhalation of carbon dioxide.

Horses and other mammals are afflicted by flies and a plethora of other insects which are nuisances and/or injurious agents. The carbon dioxide that is exhaled by a horse or other mammal is an attractant for flies and insects. A fly or other insect will come into close proximity to and/or land on an eyelid, nose and other mucosal-like membrane. A fly that stays in proximity to a horse's eye for more than three seconds will cause the horse to start flickering and flinching.

In addition to being a nuisance, flies and other insects can injure horses and mammals. They do so, inter alia, by biting and burrowing into the skin adjacent to the eyes and laying eggs in the area. Their bites and burrowing can result in bloody and/or infected sores in eyelids that in turn cause great discomfort and threaten the loss of eyesight.

U.S. Pat. No. 4,662,156 by Oettel, issued on May 5, 1987, is for an article of manufacture entitled, "Protective Mask for Animals." The patent teaches a protective mask for animals that includes a continuous one-piece screen for covering the eyes and adjacent facial areas on an animal and includes a single cutout area for the animal's ears. Both the cutout area and the portion of the mask that fits around the animal's muzzle or lower face are trimmed in a plush material.

Known in the art are insecticidal collars for animals. An insecticidal animal collar is generally a strip of flexible material that is impregnated with an insecticide and worn around the neck of the animal such that the insecticide faces the animal. The insecticide comes in contact with the hair of the animal and the insecticide slowly migrates from the strip onto the hair of the animal and then to the skin. The insecticide can cause blistering.

U.S. Pat. No. 5,003,756 by Mazzotta, Sr., issued on Apr. 2, 1991, is for an article of manufacture entitled, "Dog Garment with Flea Repelling Means." The patent teaches a dog garment comprising a coat having a size arranged to cover the chest of the dog and a portion of the neck and also to cover the sides and back of the dog, and a means on said coat arranged to hold it in place on a dog. The coat has an inner surface in engagement with the body of the dog. There is a plurality of elongated flea repelling strips. There is a plurality of holders for said flea strips mounted on the inner surface of the coat and each including a plurality of cross loops, the loops for each strip being in alignment and arranged to removably hold one of the strips. The loops are spaced from each other to expose said strip to the dog.

U.S. patent application 2008/0245315 by Tyler, published on Oct. 9, 2008, is for an article of manufacture entitled, "Pesticidal Collar With Integrated Cover." The publication discloses a multilayer laminated collar design providing protection against undesirable contact with the pesticide-bearing surface, together with suitably effective pesticidal activity. The insecticidal animal collar is formed by covering a flexible pesticidal strip component with a top cover layer that is impermeable to the pesticide. When secured around the animal, such laminated arrangement helps prevent pesticide residue from being present on the surface of the collar that is likely to come into contact with humans, furniture, or other animals.

R&R Group, LLC (Granite Bay, Calif.), sells an article of manufacture branded "Defy the Fly;" see, www.defythefly.com. This article of manufacture as best understood is believed comprised of a polyethylene end piece with snaps, a pillow fabric/cork strip center, and a polyethylene end piece with snaps. The center/middle has cork. There is a substance that has been applied to the center/middle that has as active ingredients citronella in the amount of 12%, geraniol in the amount of 8%, cedar oil in the amount 5%, glycerin/lanolin in the amount of 5% and fragrance. As an inert material, there is cork in the amount of 70%. This article of manufacture has deficiencies that include a short use period, breaks at weld to cork center, contains cork that is not biodegradable and is worn around a horse's neck behind the ears and is non-replaceable.

There is an article of manufacture branded "Fly Free Zone." This article of manufacture as best understood is believed comprised of an open-cell foam in the center (i.e., a foam rubber) and a band with Velcro at each end. There is a very thin nylon cover with large holes (about ¼" diameter). It is suspected that the article uses an insecticide. The article is worn around a horse's neck behind the ears. This article of manufacture has deficiencies that include a limited duration of use, a non-natural insecticide which requires that the article of manufacture receive U.S. Food and Drug Administration registration, the insecticides cause blistering, and the cover tears easily and is non-replaceable.

Accordingly, there exists a need for an insect repellent device that is long-lasting and that can be used for extended periods.

There exists a need for an insect repellent device that is lightweight and durable (e.g., does not tear).

There exists a need for an insect repellent device that is washable.

Accordingly, there exists a need for an insect repellent device that utilizes an all-natural insect repellent and is eco-friendly, and is replaceable after its effectiveness has worn away.

There exists a need for an insect repellent device that repels flies, mosquitoes, ticks, fleas, no-see-ums and gnats.

There exists a need for an insect repellent device that is wearable by a horse that protects the horse's skin.

There exists a need for an insect repellent device that is wearable by a horse that easily attaches to a halter or bridle.

The present invention satisfies these needs, as well as others, and generally overcomes the presently known deficiencies in the art.

SUMMARY OF THE INVENTION

The present invention is directed to an insect repellent band that is wearable by animals/mammals that has an impervious base and replaceable absorbent pad impregnated with natural oils.

An object of the present invention is an insect repellent device that repels flies, mosquitoes, ticks, fleas, no-see-ums and gnats.

An object of the present invention is an insect repellent device that is eco-friendly.

An object of the present invention is an insect repellent device that utilizes all natural insect repellent. A further object of the present invention is an insect repellent device that utilizes a blend of natural oils.

An object of the present invention is an insect repellent device that is long-lasting—up to four weeks.

An object of the present invention is an insect repellent device that is washable.

An object of the present invention is an insect repellent device that is lightweight and durable.

An object of the present invention is an insect repellent device that is wearable by a horse that easily attaches to a halter or bridle. A further object of the present invention is an insect repellent device that is wearable by a horse as a noseband.

An object of the present invention is an insect repellent device that is wearable by a horse that protects the horse's skin.

One aspect of the present invention is a repellent insert. The insert is receivable into a vented pocket and seatable in a vented compartment (discussed below). It is comprised of an absorbent pad that is typically rigid, has surface area, and has an absorbent capacity for natural oils in an amount no less than about fifty percent (50%) of the absorbent pad's dry weight such that the natural oils are retained within the pad, and such that an evaporative release of natural oils occurs at ambient temperatures. A natural oil formulation is absorbed into the absorbent pad that evaporates at ambient temperatures whereby the evaporative vapor is a repellent for flies, such that the time spent by flies within a one-foot radius of the absorbent pad is less than the time if there was no evaporation of natural oils.

Another aspect of the present invention is a vented compartment. The compartment is attachable to an article. It is comprised of a base having an upper surface, lower surface and a means for securing. An absorbent pad, as described above, is positioned between the upper surface of the base and a lower surface of a front panel (see, below). A natural oil formulation, as described above, is absorbed by the absorbent pad with an evaporative release, as described above. A front panel is mounted to the base over an absorbent pad that allows for the evaporative venting of natural oils. Optionally, the front panel can be mounted to the base such that there is an opening for the pad to be slidingly inserted and removed, thus forming a vented pocket (discussed immediately below).

Another aspect of the present invention is a vented pocket that removably receives a repellent insert. Typically, the pocket is integral with an article such as an elongated band. The pocket is characterized by an impervious back/base with a first surface and an oppositely opposed second surface. There is a front panel having a plurality of apertures, or otherwise allows diffusion of a vapor through it, that is mounted on the first side of the base/back so as to form a cavity with an opening. An absorbent pad, as described above, that is also rigid and is sized to be slidingly and removably received into the opening of the vented pocket, is positioned into the cavity of the vented pocket. A natural oil formulation, as described above, is absorbed by the absorbent pad with an evaporative release, as described above.

Another aspect of the present invention is a band having one or more vented pockets that removably receives a repellent insert. The elongated band that is comprised of at least one impervious region with an outer surface, an oppositely opposed inner surface, a first end, a second end, and at least one means for securing connected to the band. There is at least one front panel having a plurality of apertures, or otherwise allows diffusion of a vapor through it, positioned over the first side of the impervious region, and that is attached to the elongated band so as to form a vented pocket having a cavity and an opening. A repellent insert, as described above, which is also rigid and is sized to be slidingly and removably received into the vented pocket, is positioned into the cavity of the vented pocket.

Other aspects of the present invention are species of devices that have vented pockets and/or vented compartments with insect repellent inserts. An exemplary, but not limiting list of such devices are a noseband, dog collar, dog harness band, cheek band, poll band, brow band, girth band, chestplate band, wristband, hatband, ankle band, shirt, hammock, table, fly sheet, fly mask, rider's helmet, hat band, boat, tent, tail band and tie band. The vented pockets and vented compartments can be either fixedly or removably attached to a surface of the article utilizing a means for securing.

Another aspect of the present invention is a kit for a repellent tie band comprised of an elongated band with an aperture, having a vented pocket with a repellent insert or vented compartment, a stopper means for attachment to a horse's mane, tail, or other object, and a tie means for making a connection between the aperture and the stopper means.

The previously described versions of the present invention have many advantages, which include repelling black flies, mosquitoes, gnats, ticks, flees and no-see-ums; free from insecticides, utilizing a repellent comprised of substances that the U.S. Food and Drug Administration generally regards as being safe and requiring no approval from that agency; not causing blistering; being a two component system comprised of a washable, lightweight durable band (i.e., the gear) and replaceable pads, the gear being configurable to be worn on various parts of body (e.g., a nose band that attaches to a halter, and a wrist band with connecting ends); and device can be worn by mammals; namely, horses, cows, dogs and humans.

BRIEF DESCRIPTION OF THE DRAWINGS

These and other features, aspects and advantages of the present invention will become better understood with reference to the following description, appended claims and accompanying drawings where:

FIG. 3 is a schematic drawing showing the head portion of a dog wearing a collar having a vented pocket according to the present invention;

FIG. 4A is a schematic drawing showing the head portion of a horse wearing a bridle with a noseband with a vented compartment according to the present invention attached to the bridle;

FIG. 4B is a cross-sectional view of a noseband attached to a longitudinal member of a bridle taken along arrows 4A showing a wrap-around end-strap that buckles utilizing arrays of male hooks and female loops that is according to the present invention;

FIG. 5A is a schematic drawing showing the head portion of a horse wearing a bridle with a cheek band with a vented pocket according to the present invention attached to the bridle;

FIG. 5B is a cross-sectional view of a cheek band attached to a longitudinal member of a bridle taken along arrows 5A showing two perpendicular wrap-around straps that buckle utilizing arrays of male hooks and female loops that is according to the present invention;

FIG. 6 is a schematic drawing showing the head portion of a horse wearing a bridle with a poll band with a vented compartment according to the present invention attached to the bridle;

DETAILED DESCRIPTION OF THE INVENTION

Figure 1A:
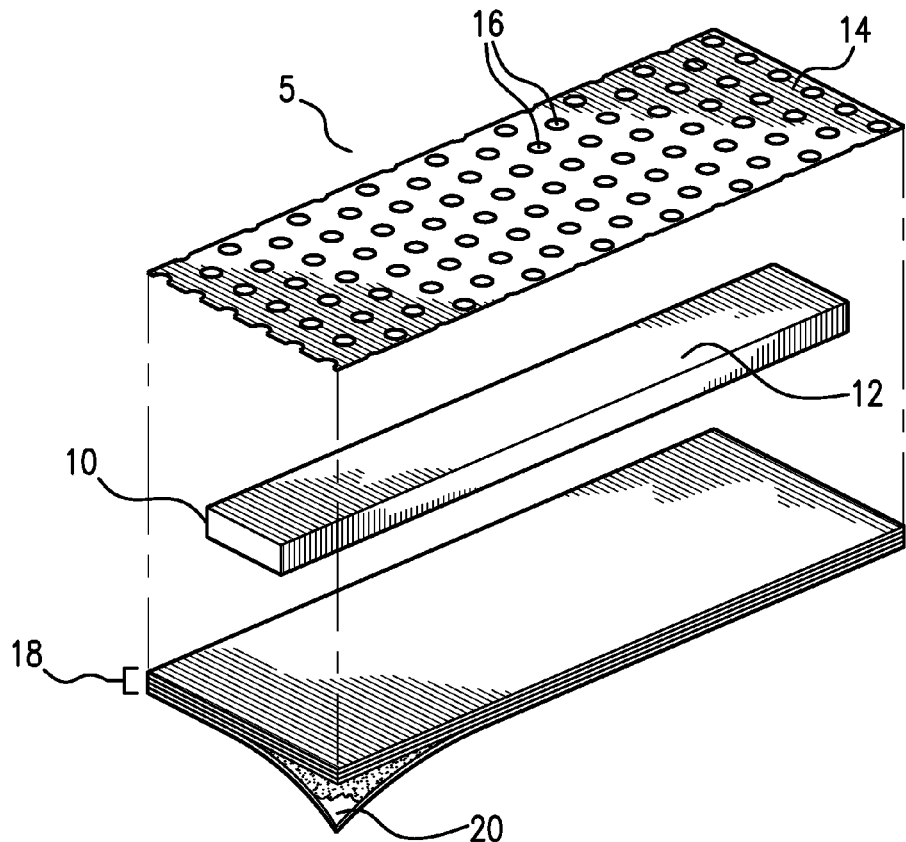
FIG. 1A is an exploded perspective view showing a vented cartridge according to the present invention.

The present invention is described more fully in the following disclosure. In this disclosure, there is a discussion of embodiments of the invention and references to the accompanying drawings in which embodiments of the invention are shown. These specific embodiments are provided so that this invention will be understood by those skilled in the art. This invention is not limited to the specific embodiments set forth herein below and in the drawings. The invention is embodied in many different forms and should be construed as such with reference to the appended claims.

This invention pertains to repelling insects from being in proximity to a host. Examples of a host include a horse, mule and other mammals used for transportation; cows, bulls and other farm mammals; dogs, cats and other household mammals that are pets; and humans. There are, inter alia, embodiments of the invention that are wearable by a host, embodiments that are attachable to an article, and embodiments that are a component of a device.

Figure 1B:
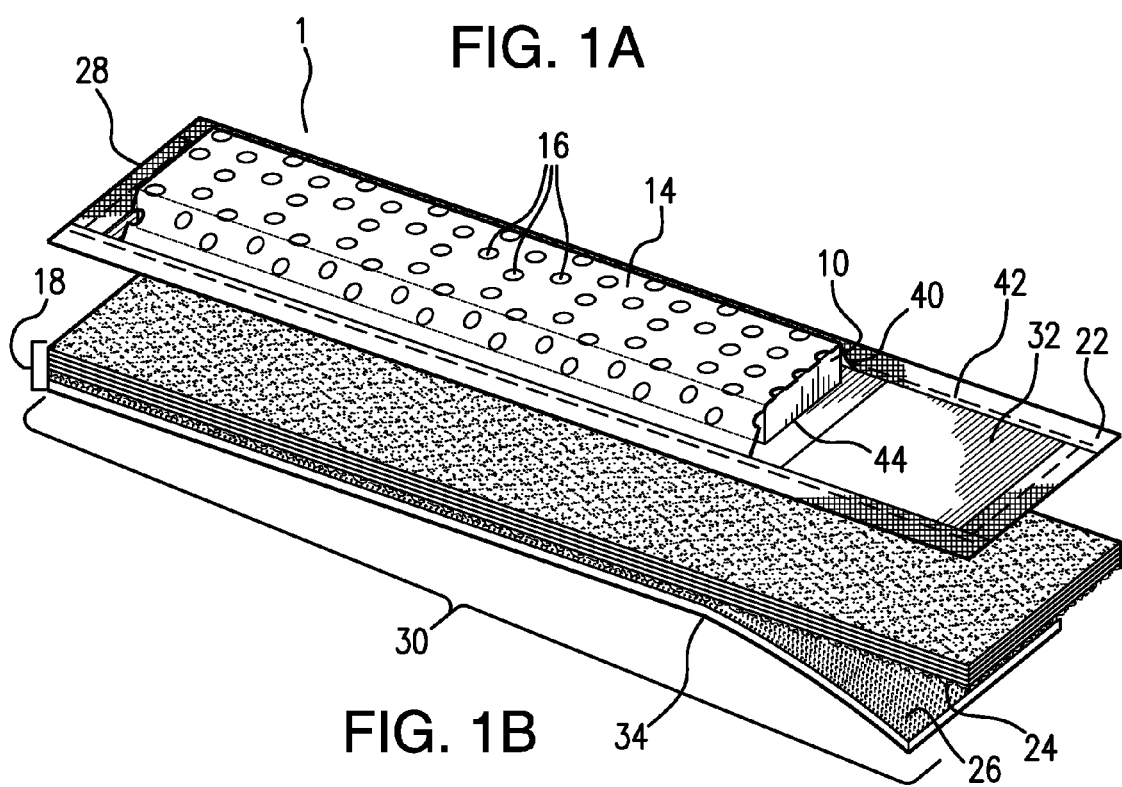
FIG. 1B is an exploded perspective view showing a vented pocket according to the present invention.

Referring to FIGS. 1A and 1B, one embodiment of the invention is a repellent insert (10) for reception into a vented pocket (1) and for being seated in a vented compartment (5) (each discussed below). The repellent insert (10) is comprised of an absorbent pad (10) and a natural oil formulation that is absorbed by or impregnated into the absorbent pad (10).

The absorbent pad (10) is a pad shaped so as to have surface area and sized so as to be receivable within a vented pocket (1) or to be seated within a vented compartment (5). Typically, the absorbent pad (10) is shaped as a parallelogram with a rectangle (i.e., an elongated strip) being a preferred parallelogram. Other shapes are suitable, such as ovals and circles. The absorbent pad can be configured to have other features, such as round edges. Generally, the use of a non-biodegradable cork filler and/or foam configuration is undesired. Typically, the absorbent pad (10) is somewhat rigid.

The absorbent pad (10) has the capacity to absorb natural oils (discussed below) with the evaporative release of natural oils at ambient temperatures. Preferably, the absorbent pad (10) absorbs natural oils in an amount no less than about fifty percent (50%) of the dry weight of the absorbent pad (10), more preferably in an amount no less than about two hundred percent (200%) of the absorbent pad's dry weight, and most preferably in an amount no less than about three hundred percent (300%) of the absorbent pad's dry weight. As discussed further below, the higher the absorption, the greater the functional longevity of a repellent insert (10).

A suitable material is cellulose fiber. A preferred material is compressed cellulosic fiber paper, and more preferably, compressed cellulosic fiber paper that has a density between about 0.279 grams (gms)/cubic centimeter (cm3) to about 0.285 gms/cm3. Compressed cellulosic fiber paper has the property of being biodegradable. Compressed cellulosic fiber paper has been used commercially in the fabrication of coasters and Christmas tree-style car deodorants, and was supplied to the market by Robert Wilson Paper Corporation (Lynbrook, N.Y.).

Continuing to refer to FIGS. 1A and 1B, typically, an absorbent pad (10) that is fabricated from compressed cellulosic fiber paper has a thickness of between about eighty-five (85) mils to about three hundred sixty (360) mils when in a dry state before the absorption of natural oils. There is expansion of the thickness of an absorbent pad (10) made from compressed cellulosic fiber papers when it is treated with natural oils; for example, an absorbent pad (10) about one-half (½) inch thick that is treated with natural oils expands to a thickness of about three-quarters (¾) inch thick. This expansion is to be taken into account when sizing a vented pocket (1) and/or a vented compartment (5) so that the absorbent pad (10) is receivable within the same.

A preferred thickness for an absorbent pad fabricated from compressed cellulosic fiber paper is about 250 mils (¼ inch) in its dry state. An absorbent pad (10) that has a thickness of a 250 mils (¼ inch) is well-suited to fit in a vented pocket (1) and/or a vented compartment (5) and is more aesthetically pleasing than a thicker or thinner absorbent pad (10). Further, a 250 mil (¼ inch) thick absorbent pad (10) has suitable pliability to be removably received in a vented pocket (1) and to bend easily as needed based on the device to which the vented pocket is mounted; for example, a dog collar (100). A compressed cellulosic fiber paper absorbent pad (10) fabricated to a thickness greater than three-eighths (⅜) of an inch generally does not result in the absorbent pad (10) holding a greater percentage amount of natural oils.

Continuing to refer to FIGS. 1A and 1B, the length and width of the absorbent pad (10) are such that there is a sufficient surface area for an effective amount (discussed below) of natural oils to be evaporatively released at ambient temperatures where a front panel (14) (discussed below) that is porous, permeable, perforated with a plurality of apertures (16), or otherwise allows diffusion through it of a vapor, is positioned over the absorbent pad (10). Consequently, the length and width of the absorbent pad (10) to constitute a sufficient surface area is configured in conjunction with configuring the porosity, permeability or perforations of the front panel (14). As a general proposition, if there is an increase in the size and density of the plurality of apertures (16) in a front panel (14), then this can allow for a greater evaporative release of natural oils such that an effective amount of natural oils can be evaporatively released with lesser dimensions of the absorbent pad (14).

The absorbent pad (10) has absorbed into it or is impregnated with a natural oil formulation. The natural oil formulation has the properties of being absorbable or impregnatable into the absorbent pad (10), evaporates at ambient temperatures, and an effective amount of evaporative vapor is a repellent for flies such that the time spent by flies within a one-foot radius of the absorbent pad (10) is less than the time if there was no evaporation of natural oils. More preferably, the natural oil formulation has the properties of being absorbable or impregnatable into the absorbent pad (10), evaporates at ambient temperatures, and an effective amount is a repellent for no less than about eighty-five percent (85%) of flies that come within a one-foot radius of the pad from staying within that radius for more than about three (3) seconds. Even more preferred, the evaporative vapor is effective to repel no less than about eighty-five percent (85%) of flies that come within a one-foot radius of the pad from staying within that radius for more than about three (3) seconds at about sixty degrees (60°) Fahrenheit and repels no less than about eighty-five percent (85%) of flies that come within a six-foot radius of the pad from staying within that radius for more than about three (3) seconds at about ninety-five degrees (95°) Fahrenheit.

The natural oil formulation is substantially comprised of natural substances that are generally regarded as safe (GRAS) by the U.S. Food and Drug Administration with other components or contaminants not having a significant adverse impact on the bio-safety of the formulation. In addition to natural oils that repel flies and/or other insects to be in proximity, optionally, the natural oil formulation can have as a component a carrier oil to help lengthen the effectiveness of the natural oils. Optionally, an encapsulation process can be utilized which exploits differences in melting temperature between additives (e.g., alcohol, carboxylic acid) and fragrance in the range of a minus twenty degrees (−20°) Celsius to fifty degrees (50°) Celsius temperature rise so as to slow down evaporation.

In a preferred embodiment, the natural oils that are selected are from the group consisting of arylessence nardus, citronella oil, methyl soyate, Texas cedarwood oil and Virginia cedarwood oil.

One natural oil formulation is nardus citronella oil in an amount between about forty-eight percent (48%) by weight to about eighty-one percent (81%) by weight, methyl soyate in an amount between about twenty-three percent (23%) by weight to about forty percent (40%) by weight, and arylessence in an amount between about two percent (2%) by weight to about four percent (4%) by weight.

Another natural oil formulation is nardus citronella oil in an amount between about thirty-six percent (36%) by weight to about sixty-one percent (61%) by weight, methyl soyate in an amount between about twenty-three percent (23%) by weight to about forty percent (40%) by weight, and Texas cedarwood oil in an amount between about fifteen percent (15%) by weight to about twenty-four percent (24%) by weight.

Another natural oil formulation is nardus citronella oil in an amount between about thirty-six percent (36%) by weight to about sixty-one percent (61%) by weight, methyl soyate in an amount between about twenty-three percent (23%) by weight to about forty percent (40%) by weight, and Virginia cedarwood oil in an amount between about fifteen percent (15%) by weight to about twenty-four percent (24%) by weight.

A more preferred natural oil formulation is nardus citronella oil in an amount between about fifty percent (50%) by weight to about eighty-four percent (84%) by weight, and Texas cedarwood oil in an amount between about twenty-five percent (25%) by weight to about forty-one percent (41%) by weight.

An even more preferred natural oil formulation is comprised of citronella oil in an amount between about forty percent (40%) by weight to about sixty-seven percent (67%) by weight, cedarwood oil in an amount between about thirty percent (30%) by weight to about forty percent (40%) by weight, and eucalyptus oil in an amount between about zero percent (0%) by weight to about thirty percent (30%) by weight.

Referring to FIG. 1A, another embodiment of the present invention is a vented compartment (5). This vented compartment (5) is fixedly or removably attachable to an article. An exemplary, but non-limiting list of articles is as follows: Referring to FIG. 3, a collar (100); referring to FIG. 4A, a noseband (200); referring to FIG. 5A, a cheek band (300); referring to FIG. 6, a poll band (400); referring to FIG. 7, a brow band (500); referring to FIG. 9, a wristband (600); referring to FIG. 10, an ankle band (700); referring to FIG. 11, a shirt (800); referring to FIG. 12, a chair (900); referring to FIG. 13, a hammock (1000); referring to FIG. 14, a table (1100); referring to FIG. 15, a fly sheet (1200); referring to FIG. 16, a rider's helmet (1300), hat (not illustrated), or hat band (not illustrated); referring to FIG. 17, a canoe or boat (1400); referring to FIG. 18, a tent (1500); and referring to FIG. 19, a tail or tie band (1600). The term "article" is meant to be construed broadly as almost anything physical that can be around flies and/or insects and includes, but is not limited to, things that are worn, things that are generally found outdoors, things that are generally used as sporting gear or while sporting, things that are furniture, and things that are water transportation contrivances.

Referring to FIG. 1A, the main components of a vented compartment (5) are a base (18) with a means for securing (18, 20), an absorbent pad (10), a natural oil formulation, and a front panel (14) that is positioned over an absorbent pad (10).

The base (18) has an upper surface, a lower surface, and a means for securing (20). Preferably, the base (18) is impervious to the natural oil formulation such that there is substantially no leaching of the natural oils through the base (18). Suitable materials for the base are vinyl, polyethylene, multi-axially oriented, high-density polyethylene, and metal. A preferred material for the base is a high-density polyethylene layer, and there can also be a metal layer. Optionally, there are additives to the base material that are ultra-violet light absorbers, mold-growth resistors, or both.

The absorbent pad (10) is as discussed above. The absorbent pad (10) is positioned on the upper surface of the base (18). A natural oil formulation as described above is absorbed or impregnated into the absorbent pad (10).

Continuing to refer to FIG. 1A, the front panel (14) is mounted to the base over an absorbent pad (10) and allows for the evaporative venting of natural oils. In a preferred embodiment, the front panel (14) is a panel that has a plurality of apertures (16). The front panel (14) is typically made from a durable vinyl that has ultra-violet light absorbers and is mold resistant. A suitable material has been supplied to the market as "coated polyvinyl," which is used mainly as outdoor banner material. The front panel (14) can be attached to the base (18) by, inter alia, stitching (see, FIG. 1B, reference numerals 22, 42), gluing, or fasteners with stitching (22, 42) being preferred. It is attached so as to create a cavity in which is seated a repellent strip (10). Optionally, the front panel can be mounted to the base such that there is an opening for the pad to be slidingly inserted and removed, thus forming a vented pocket (discussed further below).

The plurality of apertures (16) can be perforated holes. Larger-diameter apertures (16) can, but not necessarily, allow for a quicker release of natural oil vapor (scent) from the vented compartment (5). Smaller-size apertures (16) can clog up quicker from dirt; for example, dirt from a horse trail. The size (diameter) of the apertures (16) and density (number) of apertures (16) per square inch is selected so as to allow an effective amount of natural oil vapor (scent) to be released and to sufficiently keep dirt from entering the aperture (16) so that the vented compartment (5) can be in service for a desirable period without requiring washing to clean the apertures (16).

In a preferred embodiment, the front panel (14) is a panel having a plurality of apertures (16) of size and density that allows for the venting of an effective amount of natural oil vapor and retards the entry of dirt. Typically, the diameter of the apertures (16) is between about one-eighth (1/8) inch to about three-sixteenth (3/16) inch and there is a density between about thirty (30) apertures (16) per square inch to about thirty-five (35) apertures (16) per square inch.

Examples of alternative designs for the front panel (14) are a netting that allows for natural oils to diffuse through it, and a breathable fabric; namely, fabric with interwoven threads, or perforated non-woven fabric.

Continuing to refer to FIG. 1A, there is a means for securing (18, 20) that performs the function of securing the vented compartment (5) to an article (100, 200, 300, 400, 500, 600, 700, 800, 900, 1000, 1100, 1200, 1300, 1400, 1500 and 1600). The means for securing (20) can have the physical structure of a pressure sensitive adhesive layer (18). Typically, there is a release liner (20) overlay to protect the pressure sensitive adhesive until installation. Another physical structure for the means for securing is male and female fasteners that are an array of interlocking hooks to an array of loops (see, also, FIG. 1B, reference numerals 24 and 26). Such a means for securing has been supplied to the market under the brand name Velcro™ by Velcro USA Inc. (Manchester, N.H.). Another physical structure for the means for securing is a U-shaped frame that slidingly receives the compartment. Other physical structures for the means for securing are straps, buttons, clasps, snaps, two-part fasteners, penetrating fastener, and tapes. Combinations of the same can be used.

Referring to FIG. 1B, another embodiment of the present invention is a vented pocket (1). The vented pocket (1) is integral with, fixedly attachable to, or removably attachable to an article (100, 200, 300, 400, 500, 600, 700, 800, 900, 1000, 1100, 1200, 1300, 1400, 1500 and 1600). The pocket has an impervious base (18, 32), as described above, with respect to a vented compartment (5). This base (18, 32) can be a separate member, integral with the material from which an article is made, or a unique region of an article. The base (18, 32) has a first surface (32) and an oppositely opposed second surface.

There is a front panel (14) having a plurality of apertures (16), or otherwise allows diffusion of a vapor through it, as described above with respect to the vented compartment (5). The front panel (14) is positioned over the first side (32) and mounted to the base (18, 32) so as to form a cavity with an opening (40). Typically, the front panel (14) is mounted to the first side (32) of the base (18, 32) by sewing or stitching (22, 42).

A repellent strip (10), as described above, is removably receivable into the pocket (1). As discussed above, the repellent strip (10) is comprised of an absorbent pad (12). Typically, the absorbent pad (12) is slightly rigid. It is sized to be slidingly and removably received into the opening (40) of the vented pocket (1) and positioned in the cavity of the vented pocket (1). There can be a pull tab (44). A natural oil formulation, as described above, is absorbed by the absorbent pad with an evaporative release as described above.

Continuing to refer to FIG. 1B, optionally, the vented pocket (1) can have a means for securing (30) (see, also, FIG. 1A, reference numerals 18, 20), as described above. One preferred physical structure for the means for securing is an array of male hooks (26) and an array of female loops (24) with a pressure sensitive adhesive backing (34).

Figure 2A:
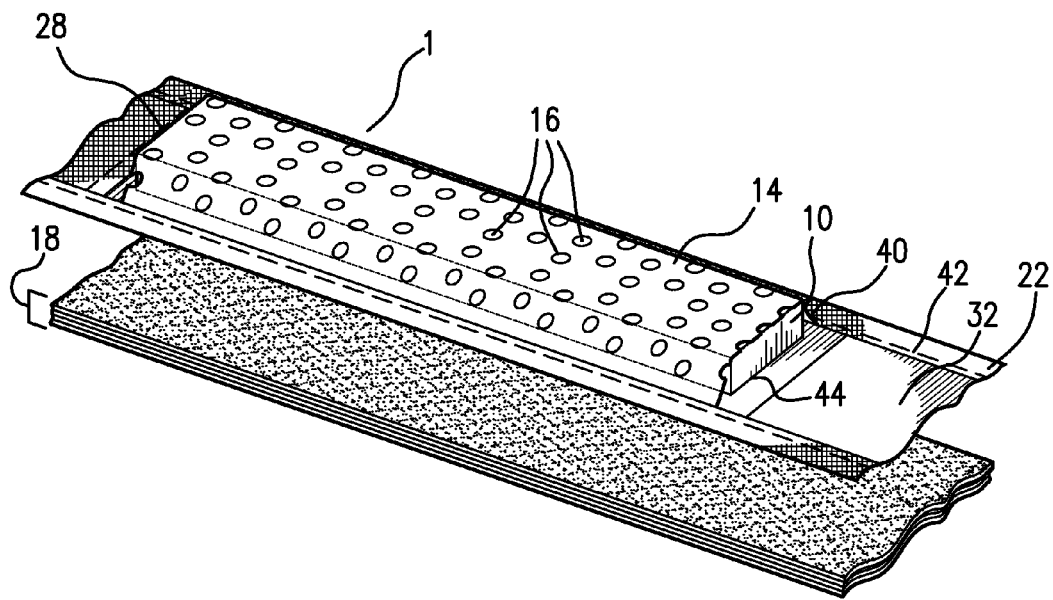
FIG. 2A is a cut-away exploded perspective view showing a band with a vented pocket according to the present invention.
Figure 2B:
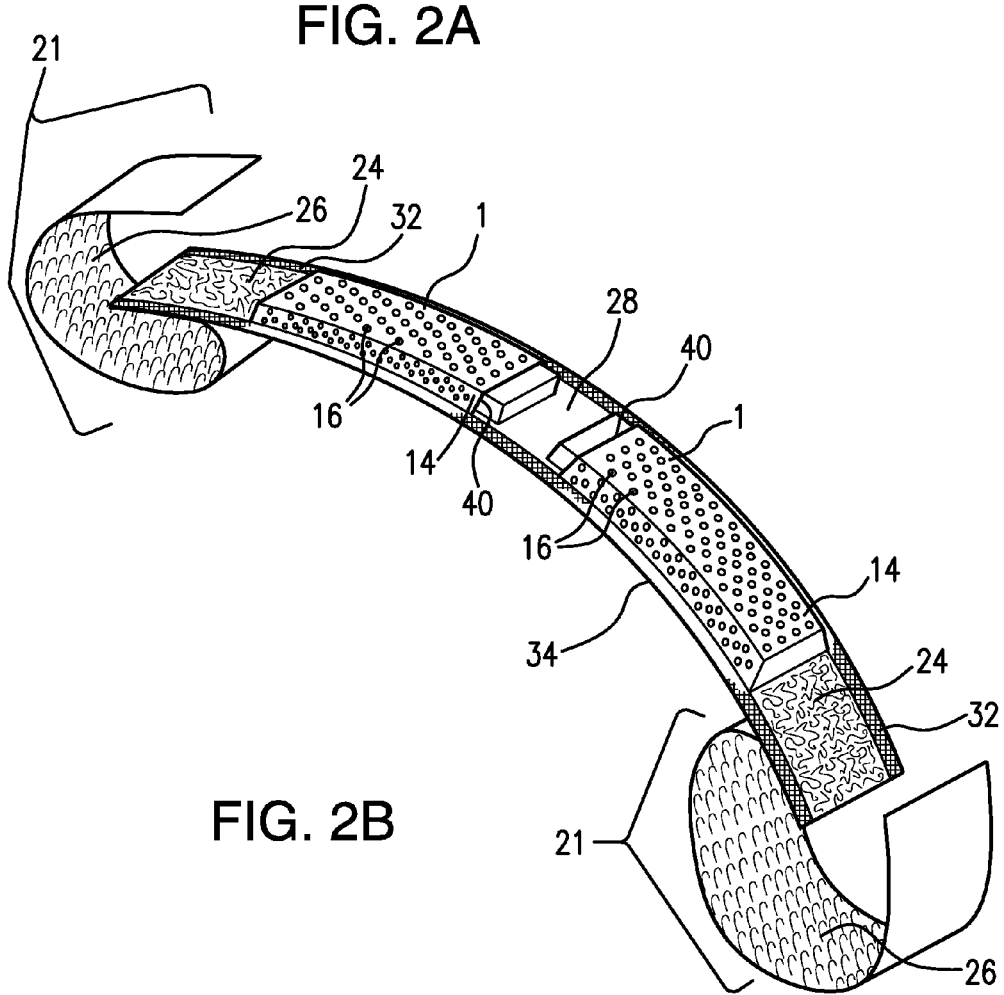
FIG. 2B is a perspective view of a band with two vented pockets and a securing means comprised of end-straps that buckle together utilizing arrays of male hooks and female loops that is according to the present invention.

Referring to FIGS. 2A and 2B, an embodiment of the invention is an elongated band (28) having one or more vented pockets (1). The elongated band (28) has length and width, an outer surface, an oppositely opposed inner surface, a first end, and a second end. Typically, it is flexible. The color of the elongated band (28) can vary. Dark colors attract flies; however, they may be more esthetically pleasing. Light colors repel flies (e.g., neon green and white); however, they may be less esthetically pleasing.

The one or more vented pockets (1) can be integral with the elongated band (28) and in which case, the entirety of the elongated band (28) is impervious or there are impervious regions corresponding to each pocket (1). In the alternative, the vented pocket (1) can be mounted on the elongated band (28) with its own impervious base (18) and the elongated band (28) need not be of an impervious material. Suitable impervious materials are discussed above.

There as at least one means for securing (21, 24, 26) connected to the band, as described above and further discussed below. A preferred means for securing (21, 24, 26) has the physical structure of a strap (21) with an array of male hooks (26) attached at each end of the band (28). Positioned on the outer surface (32) of the elongated band (28) in a region at about the ends of the elongated band (28) is an interlocking array of female loops (24). The strap (21) wraps around a longitudinal member of an article (e.g., a halter or bridle) and the arrays of male hooks (26) and female loops (24) are brought into contact with each other so as to interlock and thereby secure the elongated band (28) to the article.

In embodiments of the invention that are secured to the bridle or halter on a horse's head, the size of the elongated band (28) varies with the size of a horse's head; namely, the bigger the head size of a horse, the bigger the band. The preferred size (length and width) for horses is as follows: for an adult horse, about fifteen (15) inches long and about two (2) to three (3) inches wide.

Referring to FIG. 3, illustrated is an exemplary embodiment of the invention; that is, an elongated band (28) is fashioned to be a collar (100) for a dog and other pet mammals. The elongated band (28) has one or more vented pockets (1) formed by a front panel (14) with a plurality of apertures (16) positioned over the outer surface (32) of the elongated band (28) (i.e., the surface of the elongated band (28) that faces away from a host (a dog)). The elongated band (28) is impervious and it is this impervious inner surface that contacts the host (a dog). A repellent strip (10) is inserted into the vented pocket (1) by way of the pocket opening (40) with an overhang tab (44) for easy removal. Not illustrated is a conventional buckle system at each end of the elongated band (28) as a securing means.

Referring to FIGS. 4A and 4B, illustrated is an exemplary embodiment of the invention; that is, a noseband (200) for attachment to a bridle or halter. There is a front panel (14) having a plurality of apertures (16) positioned over the outer surface (32) of the elongated band (28) so as to form a compartment (5). A repellent strip (10) is seated in the compartment. Preferably, there are two means for securing (21) at each end of the elongated band (28).

Referring to FIG. 4B, the physical structure of the means for securing (21, 24, 26) is a strap (21) at each end of the elongated band (28) with an array of male hooks (26). There is an array of female loops (24) on the outer surface (32) of the elongated band (28) in a region near each end. The strap (21) wraps around a longitudinal of the bridle or halter member in the direction of arrows 4A and the array of male hooks (26) removably interlocks with the array of female loops (24).

Referring to FIGS. 5A and 5B, illustrated is an exemplary embodiment of the present invention; that is, a cheek band (300) for attachment to a bridle or halter. The elongated band (28) is made from an impervious material. The cheek of a horse cheek wearing the band (300) contacts the inner surface of the band (300), which is impervious. On the outer surface (32) is a vented pocket (1). The vented pocket (1) is comprised of a front panel (14) having apertures (16) that is attached to the outer surface (32) so to form a pocket having an opening (40). A repellent insert (10) comprised of a pad (12) is inserted into the pocket (1) such that there is an overhang tab (44) by which to pull out and replace worn out repellent insert (10) while the cheek band (300) is attached to a bridle or halter.

Referring to FIG. 5B, there is a means for securing (21, 24, 26) at each of the cheek band (300). A preferred physical structure of the means for securing (21, 24, 26) is a pair of straps (21) at about the end of the elongated band (28) which extend out perpendicular to the longitudinal axis of the elongated band as shown by arrows 5A. At about the end of one of the straps (21) is an array of male hooks (26) and at about the end of the other strap (21) is an array of female loops (24). The straps (21) wrap under a longitudinal member of the bridle or halter member in a direction perpendicular to arrows 5A and the array of male hooks (26) removably interlocks with the array of female loops (24) so as to secure the cheek band (300) to the halter or bridle.

Referring to FIG. 6, illustrated is an exemplary embodiment of the present invention; that is, a poll band (400) for attachment to a bridle or halter. In this embodiment, there is a vented compartment with a front panel (14) having a plurality of apertures (16) positioned over the outer surface (32) of the elongated band (28). The elongated band (28) is impervious in its entirety and an impervious surface contacts the horse.

Figure 7:
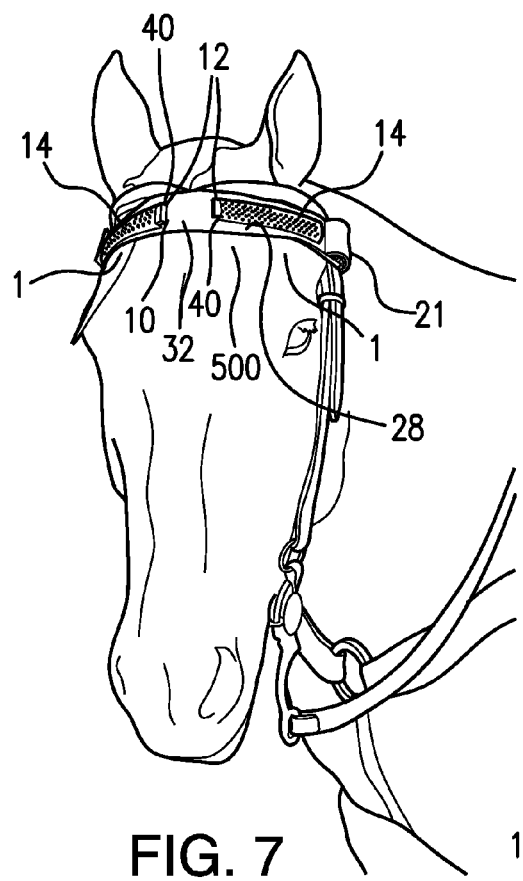
FIG. 7 is a schematic drawing showing the head portion of a horse wearing a bridle with a brow band with two vented pockets according to the present invention attached to the bridle.

Referring to FIG. 7, illustrated is an exemplary embodiment of the present invention; that is, a brow band (500) for attachment to a bridle or halter. There is illustrated in this embodiment, a first and a second vented pocket (1) formed by a first and a second front panel (14) having a plurality of apertures positioned over the outer surface (32) of the elongated band (28). Each of the pockets (1) has a pocket opening (40) of approximately one-quarter (¼) inch so as to receive a repellent insert (10). The elongated band (28) is impervious in its entirety, and the impervious surface faces towards the horse. There is means for securing at the end of the brow band (500) having the physical structure of a wrap-around strap (21) along with interlocking arrays of hooks and loops.

Figure 8:
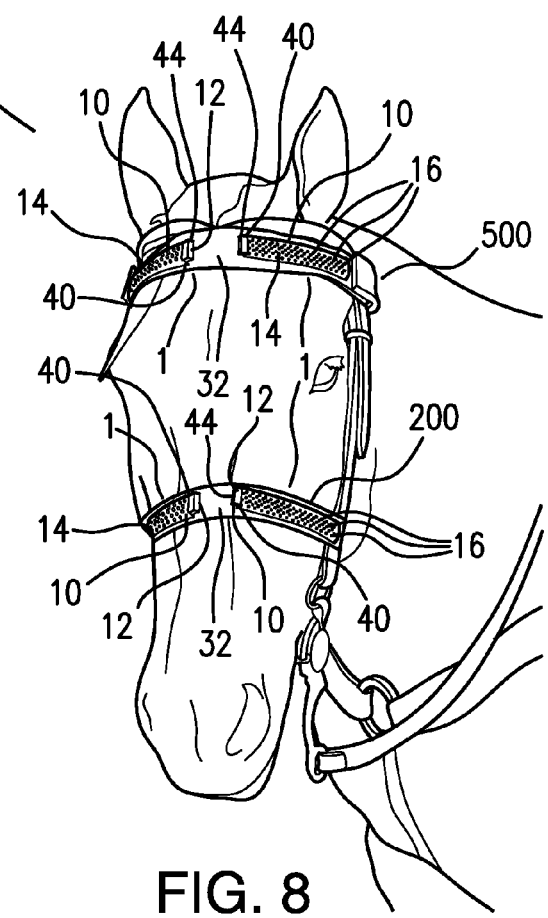
FIG. 8 is a schematic drawing showing the head portion of a horse wearing a bridle with a brow band and a noseband with vented pockets that are each according to the present invention that are each attached to the bridle.

FIG. 8 illustrates exemplary embodiment of a horse wearing both a brow band (500) and a noseband (200) attached to a bridle or halter. Each band (200, 500) on the outer surface (32) has two vented pockets (1) with front panels (14) having apertures (16) and a pocket opening (40) of approximately one-quarter (¼) inch to receive and replace worn repellent inserts (10), as discussed above. The absorbent pad (12) is sized long enough that there is a pull tab (44) overhang to facilitate removal.

Figure 9:
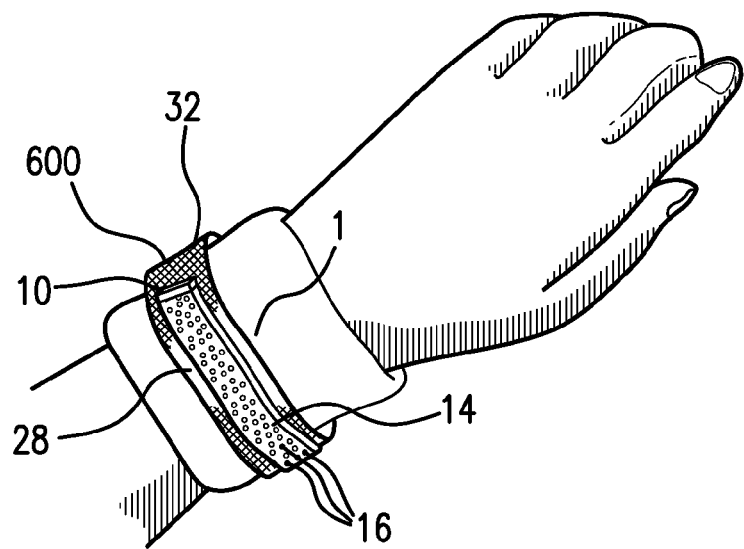
FIG. 9 is a schematic drawing showing the wrist and hand portion of a person wearing a wristband with a vented pocket according to the present invention.

Referring to FIG. 9, illustrated is an exemplary embodiment of the present invention; that is, a wristband (600) with a vented pocket (1) formed by front panel (14) with apertures (16) being attached to an outer surface (32) of a band (28). The length of time between removing and replacing worn out repellent inserts (10) may depend on the degree of sweating by the user and said sweat contacting the insert (10).

Figure 10:
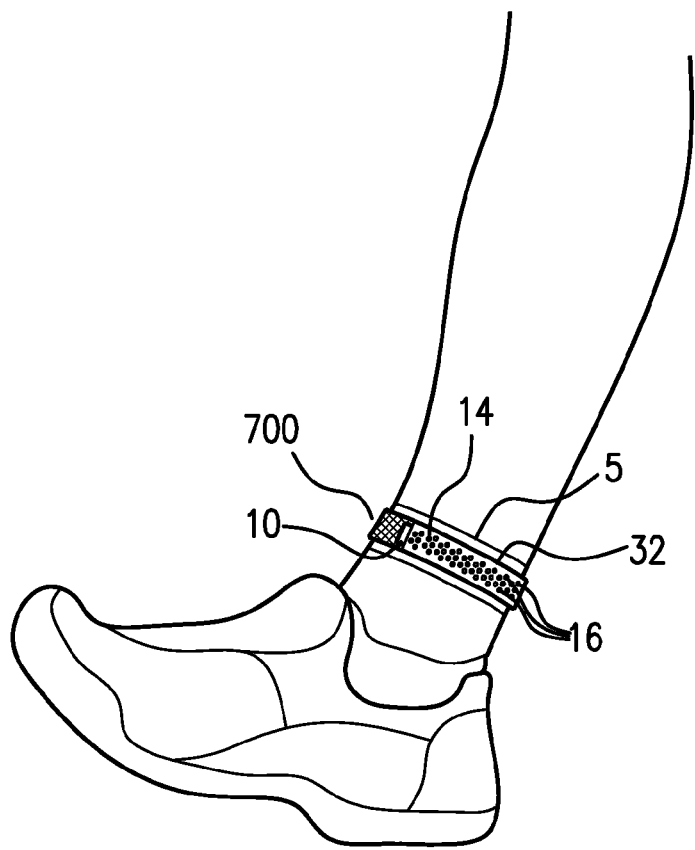
FIG. 10 is a schematic drawing showing the lower leg and foot portion of a person wearing an ankle band with a vented pocket according to the present invention.

Referring to FIG. 10, illustrated is an exemplary embodiment of the present invention; that is, an ankle band (700). The front panel (14) is sized so as to form a vented pocket (1) that conformingly and snugly receives a repellent insert (10) so that it does not fall out from the motion and impact of walking or running.

Figure 11:
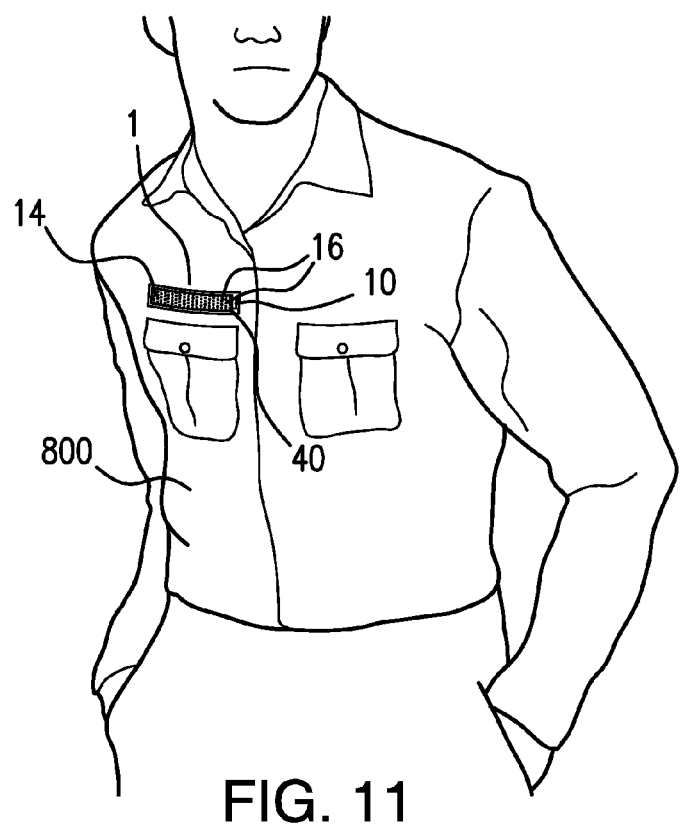
FIG. 11 is a schematic drawing showing the upper body portion of a person wearing a shirt with a repellent pocket according to the present invention.

Referring to FIG. 11, illustrated is an exemplary embodiment of the present invention; that is, a shirt (800) with a vented pocket (1) comprised front panel (14) with apertures (16) and an impervious base that is not visible in the illustration. It is envisioned that this shirt would be worn by golfers, fishermen, gardeners and others such that the user desires that the vented pocket (1) not be noticeable and/or an annoyance. Accordingly, the repellent insert (10) is sized to be thin and made of compressed cellulosic fiber paper with a high uptake capacity so that enough natural oil formulation is absorbed or impregnated to repel flies and/or other insects.

Figure 12:
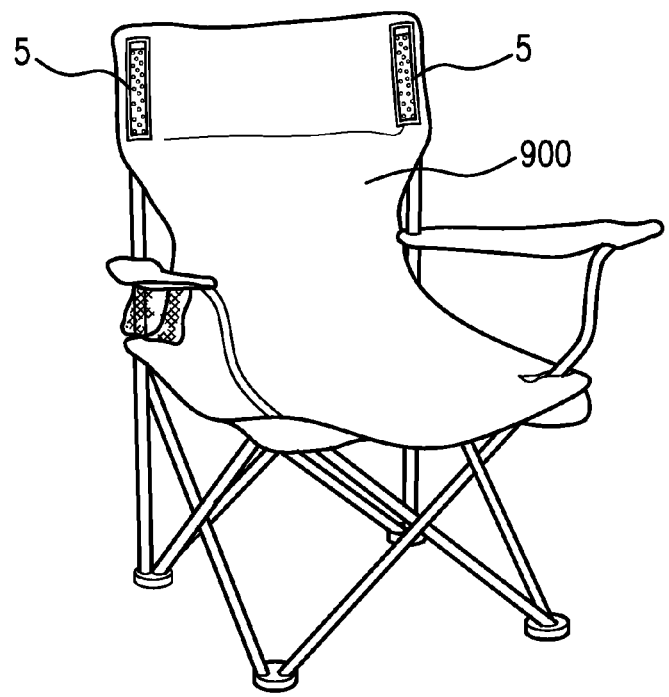
FIG. 12 is a schematic drawing showing a chair with vented pockets according to the present invention.

Referring to FIG. 12, illustrated is an exemplary embodiment of the present invention; that is, a chair (900) with vented compartments (5) attached to the chair (900). Each compartment (5) has an impervious base so that the natural oil formulation does not leach into the chair (900) to spoil it. There is a front panel having a plurality of apertures so that the natural oil formulation can be evaporatively released.

Figure 13:
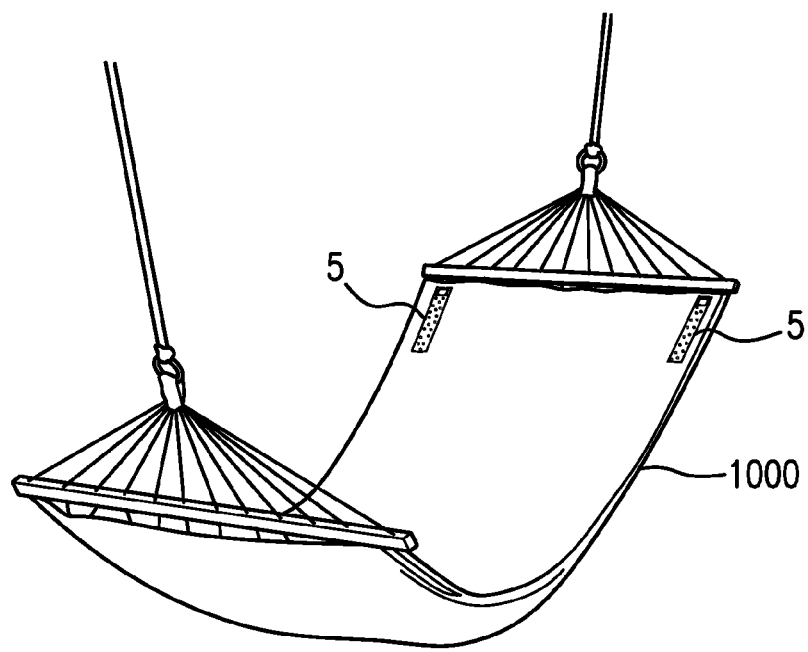
FIG. 13 is a schematic drawing showing a hammock with vented pockets according to the present invention.

Referring to FIG. 13, illustrated is an exemplary embodiment of the present invention; that is, a hammock (1000) with vented compartments (5) attached to it. Each compartment (5) has an impervious base so that the natural oil formulation does not leach into the hammock (1000) to spoil it. There is a front panel having a plurality of apertures so that the natural oil formulation can be evaporatively released.

Figure 14:
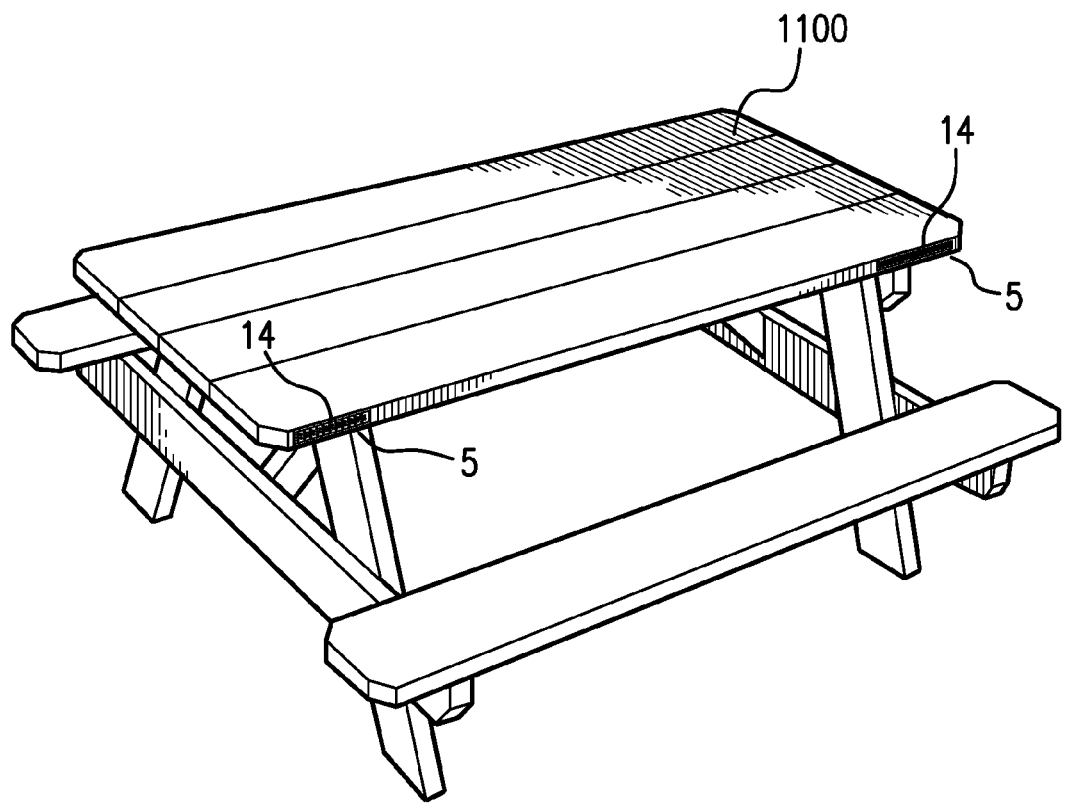
FIG. 14 is a schematic drawing showing a picnic table with vented cartridges according to the present invention.

Referring to FIG. 14, illustrated is an exemplary embodiment of the present invention; that is, a table (1100) with vented compartments (5) attached to it. Each compartment (5) has an impervious base (not visible) so that the natural oil formulation does not leach into the chair (900) to spoil it. There is a front panel (14) having a plurality of apertures so that the natural oil formulation can be evaporatively released.

Figure 15:
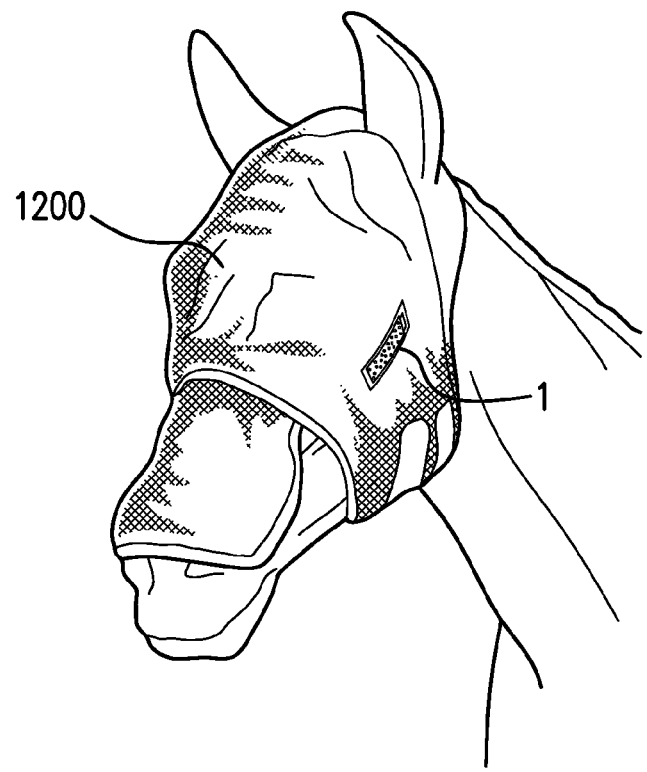
FIG. 15 is a schematic drawing showing the head portion of a horse wearing a fly sheet with a vented pocket according to the present invention.

Referring to FIG. 15, illustrated is an exemplary embodiment of the present invention; that is, a fly sheet (1200) with a vented pocket (1). With one vented pocket (1), this fly sheet is for use with temperatures around ninety degrees (90°) Fahrenheit. At cooler temperatures, more pockets would be secured to the fly sheet (1200).

Figure 16:
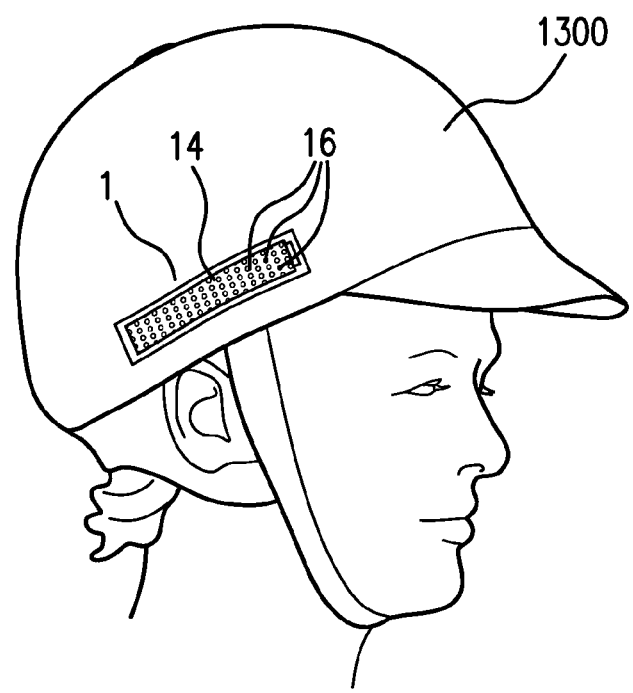
FIG. 16 is a schematic drawing showing the head portion of a horse rider wearing a rider's helmet with a vented pocket according to the present invention.

Referring to FIG. 16, illustrated is an exemplary embodiment of the present invention; that is, a rider's helmet (1300), a hat (not illustrated) or a hat band (not illustrated) with a vented pocket (1) attached to the helmet (1300), hat (not illustrated), or hat band (not illustrated). The pocket (1) has a front panel (14) with apertures (16). Alternatively, a vented compartment (5) is attached to the helmet (1300), hat (not illustrated), or hat band (not illustrated) instead of a vented pocket (1).

Figure 17:
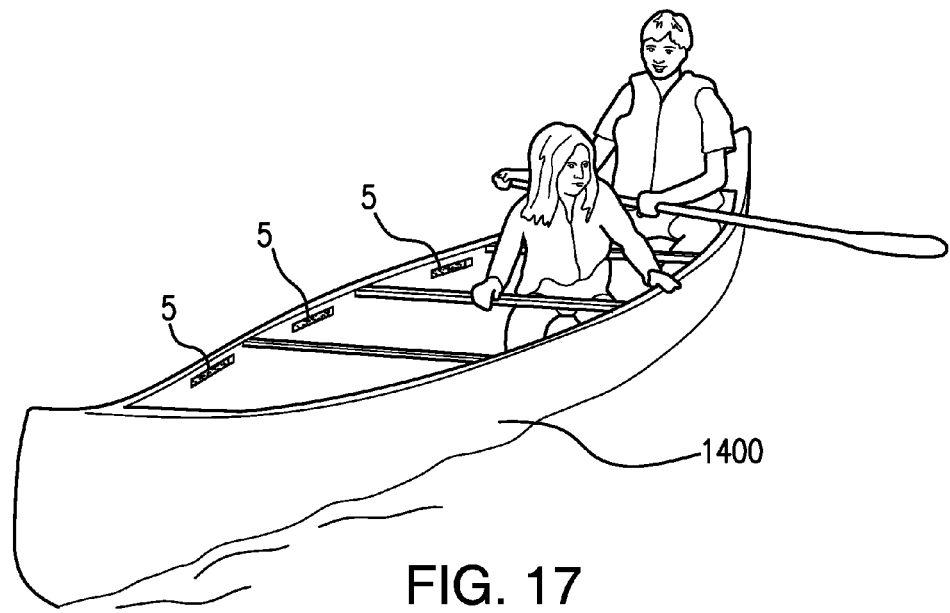
FIG. 17 is a schematic drawing showing a canoe with vented cartridges according to the present invention.

Referring to FIG. 17, illustrated is an exemplary embodiment of the present invention; that is, a boat (1400) with a plurality of vented compartments (5) attached to it.

Figure 18:
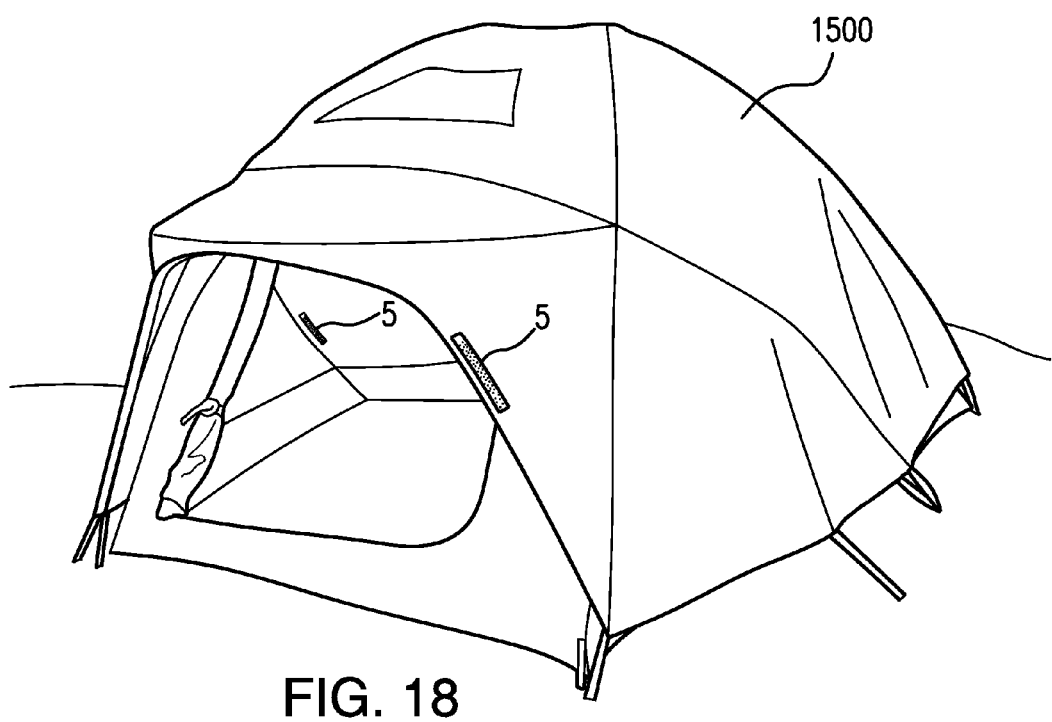
FIG. 18 is a schematic drawing showing a tent with vented cartridges according to the present invention.

Referring to FIG. 18, illustrated is an exemplary embodiment of the present invention; that is, a tent (1500) with a plurality of vented compartments (5) attached to it.

Figure 19:
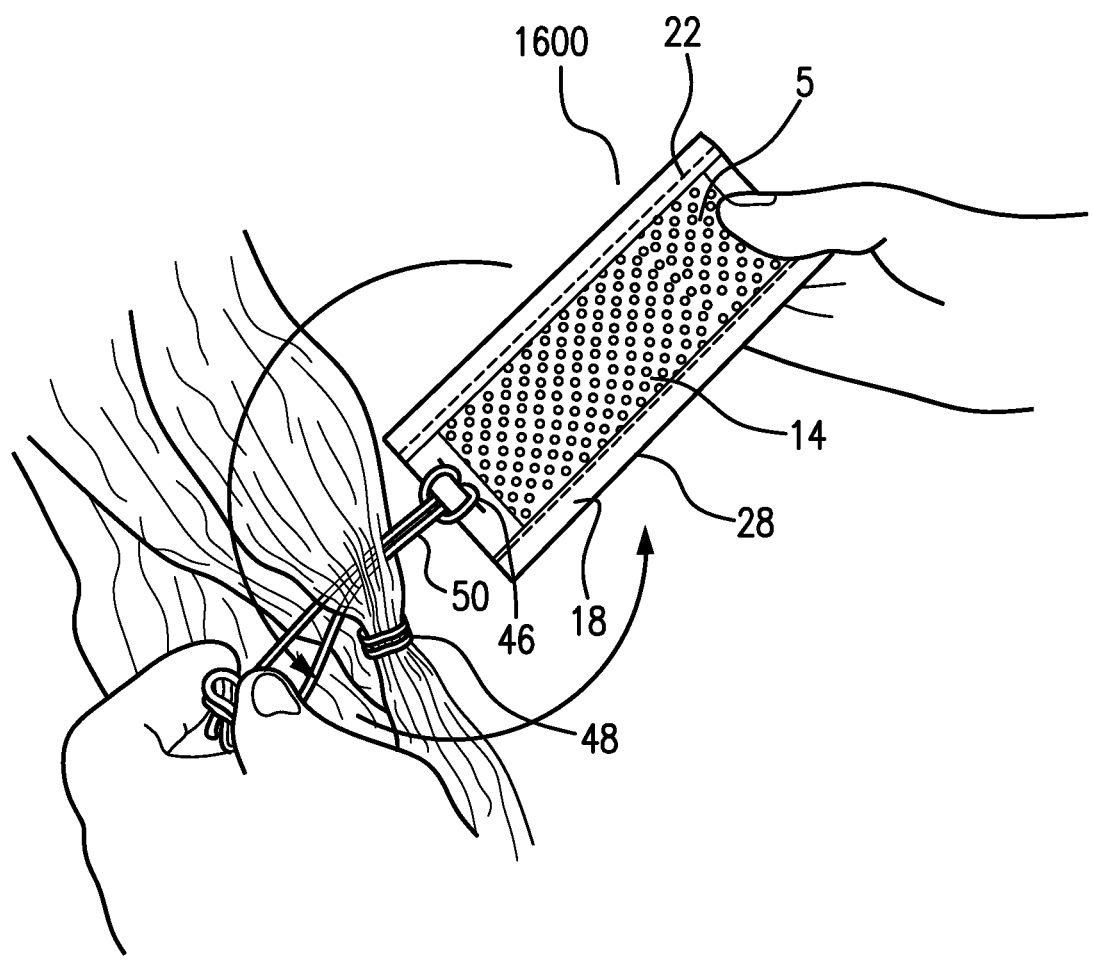
FIG. 19 is a schematic drawing showing the tail portion of a horse with a tail band according to the present invention.

Referring to FIG. 19, illustrated is an exemplary embodiment of the present invention; that is, a tie band kit installed on a horse's tail. The kit (1600) is comprised of a band (28) with a vented compartment (5) or vented pocket (1), a stopper means (48) and a tie (50).

Preferably, the band (28) has a tri-layer impervious base (18) as described above so that the natural oil formulation does not leach out onto an installer's hand or the horse's tail. A repellent insert (not visible) is seated on the impervious base. A top panel (14) is sewn (22) to the impervious base (18). At about one end of the band (28), there is an aperture (46). This aperture (46) can be in the shape of slit.

The tie (50) is a cord or string that may be elastic or inelastic, and that is configurable into a closed loop with the aid of a fastener or by knotting.

The stopper means (48) performs two functions. One function is to be attachable to tail hairs, mien hairs or other circumscribable member of a host or article. The other function is to stop sliding of a looped tie around said tail hairs, mien hairs or other circumscribable member. Physical structures of the stopper means include a rubber band, string, collar, clamp, band and cord.

To use the kit, one end of the looped tie (50) is inserted into the aperture (46) and the other free end of the looped tie (50) is then passed through the interior of the loop so to lock the tie (50) through the aperture (46) whereby the band (28) is secured to the tie. A stopper means (48) is affixed to tail hairs, mien hairs or other circumscribable member of a host or article. The free end of the looped tie (50) is passed under the tail hairs, mien hairs or other circumscribable member of a host or article just above the stopper means (48). The band (28) is then passed over the tail hairs, mien hairs or other circumscribable member of a host or article and inserted into the interior of the looped tie (50)) and pulled taut about the tail hairs, mien hairs or other circumscribable member of a host or article so to secure the tie (50). The stopper means (48), restricts the tie (50) from sliding down off the tail hairs, mien hairs or other circumscribable member of a host or article.

A method of manufacturing the device is utilizing sewing to attach and connect the various components and parts. The absorbent pad (12) is impregnated with and/or has absorbed into it a natural oil formulation to make a repellent insert (10). Typically, the device is packaged without repellent inserts (10), and a starter set of repellent inserts (10) are put in a separate aluminized bag.

The device is wearable by a host that is a mammal. The device protects both animals and humans. The device is suited for cats, cows, dogs, horses and humans. The manner of use varies with the host. With a horse, a device fits/slides over horse's muzzle, attaches to a bridle or halter, and sits in the middle of the muzzle between eyes and nose. The device is secured to the halter or bridle in such a way that while a horse is grazing, it does not slide down leaving the horse's eyes unprotected. For humans, embodiments of the invention are worn, inter alia, as wristbands, forearm bands, ankle bands, hat bands, or free hanging from a belt. For dogs and cows, embodiments of the invention are worn, inter alia, as collars, free hanging from collars, or as leg bands.

A repellent insert (10) impregnated with oils has a service life of about four (4) weeks depending on weather conditions and in particular, temperature. Longevity has an inverse relationship with temperature and the distance range of effectiveness has proportional relationship with temperature. As temperature increases, the natural oils vaporize more strongly. Hence, the repellent insert (10) has a greater distance range of effectiveness and a shorter service life. At lower temperatures, the repellent insert (10) has a shorter distance range of effectiveness and a longer service life. At a temperature of about sixty degrees (60°) Fahrenheit, a repellent insert (10) has about a one (1) foot radius of effectiveness; and at a temperature of between about ninety degrees (90°) to about one hundred degrees (100°) Fahrenheit, a repellent insert (10) has a radius of effectiveness of about six (6) feet.

There is an inverse proportional relationship between the number of repellent compartments (5) to be attached to an article and temperature. At about sixty degrees (60°) Fahrenheit, several repellent compartments (5) need be attached to an article for a desired effect. At about ninety degrees (90°) to about one hundred degrees) (100°) Fahrenheit, only one repellent compartment (5) may need to be attached to an article for a desired effect.

When the pads are no longer effective and/or after about four (4) weeks, the absorbent pads can be replaced. The device is washed periodically to clean and open the plurality of apertures. Typically, the device is washed when the pads are removed, because detergent has an adverse impact on the natural oils.

The previously described versions of the present invention have many advantages. One advantage is that the device is comprised of gear that utilizes replaceable pads such that the device is long lasting, durable and washable. That is, the device can be used repeatedly by changing the pads, the device can be washed, and it is durable such that it resists falling apart. Another advantage is that the device is eco-friendly, utilizing an all-natural repellent free from insecticides and biodegradable pads that are free from cork and foam. A further advantage is that the repellent formulation is comprised of oils that are generally regarded as safe (GRAS) by the U.S. Food and Drug Administration (FDA) and no registration is required. Another advantage is an impermeable backing that protects horse, human, or other host from the leakiness and/or leaching of a repellent; notwithstanding that the repellent formulation is all natural.

EXAMPLES

The following examples further describe and demonstrate embodiments within the scope of the present invention. The examples are given solely for the purpose of illustration and are not to be construed as limitations or restrictions of the present invention, as persons skilled in the art will quickly realize many variations thereof are possible that are all within the spirit and scope of the invention.

Example 1

Example 1 is an example of a natural oil formulation. The formulation is comprised of about 64.5 percent by weight nardus citronella oil, about 32.25 percent by weight methyl soyate, and about 3.25 percent by weight arylessence.

Example 2

Example 2 is an example of a natural oil formulation. The formulation is comprised of about 48.4 percent by weight nardus citronella oil, about 32.2 percent by weight methyl soyate, and about 19.4 percent by weight Texas cedarwood oil.

Example 3

Example 3 is an example of a natural oil formulation. The formulation is comprised of about 48.4 percent by weight nardus citronella oil, about 32.2 percent by weight methyl soyate, and about 19.4 percent by weight Virginia cedarwood oil.

Example 4

Example 4 is an example of a natural oil formulation. The formulation is comprised of about 67.0 percent by weight nardus citronella oil, and about 33.0 percent by weight Texas cedarwood oil.

Example 5

Example 5 is an example of a natural oil formulation. The formulation is comprised of about 48.4 percent by weight nardus citronella oil, about 32.2 percent by weight methyl soyate, and about 19.4 percent by weight Virginia cedarwood oil.

Example 6

Example 6 is efficacy testing. Efficacy testing was conducted as follows: A natural oil formulation was mixed comprised of about 66⅔ percent by weight citronella and about 33⅓ percent by weight cedarwood oil. The environment was at a temperature of between about sixty degrees (60°) to about sixty-five degrees (95°) Fahrenheit. Bands according to the present invention were field tested by securing them to the halters and bridles of five (5) horses. The horses were observed while on the race track or in their stalls at rest for eight (8) to ten (10) hours. During this time period, twenty (20) to thirty (30) flies landed on these five (5) horses, which flies stayed on the horses for more than three (3) seconds. This compares to hundreds of flies that landed continuously on the control horses not wearing bands, and which flies stayed on the horses continuously for more than three (3) seconds.)

Example 7

Example 7 pertains to longevity testing. Longevity testing was conducted as follows: Absorbent pads (12) impregnated with natural oils were weighed on day one (1) and after twenty-eight (28) days of accelerated aging in an oven and at ambient temperature aging of between about sixty degrees (60°) Fahrenheit to about seventy degrees) (70°) Fahrenheit by sitting outside as naked pads on an impermeable substrate material. The pads in the oven lost about forty percent (40%) of their weight over eight (8) days, and the pads sitting outside lost between seventy-five percent (75%) and ninety-five percent (95%) of their weight after four (4) weeks.

Example 8

Example 8 is an effectiveness testing example of a repellent insert. A natural oil formulation was mixed comprised of about 66⅔ percent by weight citronella and about 33⅓ percent by weight cedarwood oil. A compressed cellulosic fiber paper absorbent pad had absorbed into it the natural oil formulation in an amount of about three hundred percent (300%) of the pad's weight. A horse was vigorously worked out wearing a 4'×3' (four feet by three feet) saddle pad. After the workout, there was sweat and lather over the entire surface of the saddle pad. The saddle pad was laid down in an open environment at a temperature of between about ninety degrees (90°) to about ninety-five degrees (95°) Fahrenheit in a place where several hundred flies were attracted to it. The aforementioned repellent insert was positioned at about the center of the saddle pad. Within about one (1) to about five (5) seconds, all but a small number of flies left the blanket, and after about fifteen (15) seconds no flies remained.

Although the present invention has been described in considerable detail with reference to certain preferred versions thereof, other versions are possible with substituted, varied and/or modified materials and steps employed. These other versions do not depart from the invention. Therefore, the spirit and scope of the appended claims should not be limited to the description of the preferred versions contained herein.

What is claimed:

1. A repellent insert for reception into a vented pocket, such insert being comprised of:
   a) an absorbent pad comprised of compressed cellulosic fiber that is slightly rigid, has surface area and has an absorbent capacity for natural oils in an amount no less than about two hundred percent (200%) of the absorbent pad's dry weight such that the natural oils are retained within the pad and such that an evaporative release of natural oils occurs at ambient temperatures; and
   a natural oil formulation an oil formulation comprising about 40 to about 67 percent by weight citronella oil; about 30 to about 40 percent by weight cedarwood oil and 0.00 to 30 percent by weight eucalyptus oil absorbed on said pad,
   whereby, said repellant insert is operatively receivable into a vented pocket wherein said oil formulation evaporates at ambient temperatures and said insert is a repellent for flies such that the time spent by flies within a one-foot radius of the absorbent pad is less than the time if there was no evaporation of natural oils.

2. A vented compartment that is attachable to an article, such vented compartment being comprised of:
   a) a base having an upper surface, a lower surface and means for securing;
   b) an absorbent pad comprised of compressed cellulosic fiber that is positioned on the upper surface and has an absorbent capacity for natural oils in an amount no less than about two hundred percent (200%) of the absorbent pad's dry weight, such that the natural oils are retained within the pad and such that an evaporative release of natural oils occurs at ambient temperatures;
c) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad and
d) a front panel that is mounted to the base over the absorbent pad that allows for the evaporative venting of natural oils wherein said oil formulation evaporates at ambient temperatures and said insert is a repellent for flies such that the time spent by flies within a one-foot radius of the absorbent pad is less than the time if there was no evaporation of natural oils.

3. The vented compartment of claim 2 where the base is an impervious high-density polyethylene.

4. The vented compartment of claim 2 where the front panel is mounted to the base with an opening between the front panel and base such that the absorbent pad can be slidingly inserted and removed from between the front panel and base.

5. The vented compartment of claim 2 where the means for securing is selected from the group consisting of strapping with an array of male hooks that removably interlock with an array of female loops, a pressure sensitive adhesive, a snap, a buckle and combinations of the same.

6. A vented compartment that is attachable to an article, such vented compartment being comprised of:
a) an impervious base of high-density polyethylene that forms an upper surface and lower surface and a means for securing;
b) an absorbent pad that is positioned on the upper surface comprised of compressed cellulosic fiber paper having a density of between about 0.279 gms/cm$^3$ to about 0.285 gms/cm$^3$, and a thickness of between about eighty-five (85) mils to about three hundred sixty (360) mils, such that natural oils in an amount no less than about three hundred percent (300%) of the absorbent pad's dry weight are retained within the pad and such that an evaporative release of natural oils occurs at ambient temperatures and the absorbent pad is positioned into the vented pocket;
c) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad; and
d) a front panel that is mounted to the base over the absorbent pad that has a plurality of apertures that allows for the evaporative venting of an effective amount of natural oils and retards the entry of dirt wherein said oil formulation evaporates at ambient temperatures and said insert is a repellent for flies such that the time spent by flies within a one-foot radius of the absorbent pad is less than the time if there was no evaporation of natural oils.

7. The vented compartment of claim 6 where the means for securing is selected from the group consisting of strapping with an array of male hooks that removably interlock with an array of female loops, a pressure sensitive adhesive, a snap, a buckle and combinations of the same.

8. The vented compartment of claim 6 where the front panel is mounted to the base with an opening between the front panel and base such that the absorbent pad can be slidingly inserted and removed from between the front panel and base.

9. A band characterized by a vented pocket that removably receives a repellent insert, such band being comprised of:
a) an elongated band comprised of at least one impervious region with an outer surface, an oppositely opposed inner surface, a first end, a second end and at least one means for securing connected to the band;
b) at least one front panel having a plurality of apertures positioned over a first side that is attached to the elongated band so as to form a vented pocket having an opening;
c) an absorbent pad comprised of compressed cellulosic fiber that is rigid, has surface area, has an absorbent capacity for natural oils in an amount no less than about two hundred percent (200%) of the absorbent pad's dry weight such that the natural oils are retained within the pad and such that an evaporative release of natural oils occurs at ambient temperatures, is sized to be slidingly and removably received into the vented pocket through the opening and positioned into the vented pocket; and
d) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad wherein said oil formulation evaporates at ambient temperatures and said insert is a repellent for flies such that the time spent by flies within a one-foot radius of the absorbent pad is less than the time if there was no evaporation of natural oils.

10. The band of claim 9 where the absorbent pad is sized to overhang the vented pocket when positioned fully into the vented pocket so as form a pull tab.

11. The band of claim 9 where the impervious region is comprised of a 3-ply laminate having an aluminum core surrounded by two layers of multi-axially oriented, high-density polyethylene that form the first side and a second side.

12. The band of claim 9 where the front panel has a plurality of apertures of a size and density that allows for the release of an effective amount of natural oil vapor and retards the entry of dirt.

13. The band of claim 9 where the means for securing is selected from the group consisting of strapping with an array of male hooks that removably interlock with an array of female loops, a pressure sensitive adhesive, a snap, a buckle and combinations of the same.

14. The band of claim 9 where there is a first means for securing connected to the first end of the band and a second means for securing that is connected to the second end of the band.

15. A band characterized by a vented pocket that removably receives a repellent insert, such band being comprised of:
a) an elongated band comprised of at least one impervious region that is comprised of high-density polyethylene, an outer surface, an oppositely opposed inner surface, a first end, a second end and at least one means for securing connected to the band;
b) at least one front panel having a plurality of apertures positioned over the first side that is attached to the elongated band so as to form a vented pocket having an opening;
c) an absorbent pad comprised of compressed cellulosic fiber paper having a density between about 0.279 gms/cm$^3$ to about 0.285 gms/cm$^3$, having a thickness of between about eighty-five (85) mils to about three hundred sixty (360) mils that is rigid, has surface area, has an absorbent capacity for natural oils in an amount no less than about three hundred percent (300%) of the absorbent pad's dry weight such that the natural oils are retained within the pad and such that an evaporative release of natural oils occurs at ambient temperatures, sized to be slidingly and removably received into the vented pocket through the opening and positioned into the vented pocket; and d) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad wherein said oil formulation evaporates at ambient temperatures and said insert is a repellent for flies such that the time spent by flies within a one-foot radius of the absorbent pad is less than the time if there was no evaporation of natural oils.

16. The band of claim 15 where the absorbent pad is sized to overhang the vented pocket when positioned fully into the vented pocket so as form a pull tab.

17. The band of claim 15 where the means for securing is selected from the group consisting of strapping with an array of male hooks that removably interlock with an array of female loops, a pressure sensitive adhesive, a snap, a buckle and combinations of the same.

18. The band of claim 15 where there is a first means for securing connected to the first end of the band and a second means for securing that is connected to the second end of the band.

19. The band of claim 15 hosted on a host selected from the group consisting of cats, cows, dogs, horses and humans.

20. The band of claim 15 hosted on a host that is a horse.

21. A device that is an insect repellent noseband that is attachable to a bridle or a halter, such device being comprised of:
   a) an elongated band comprised of high-density polyethylene that forms a first side and oppositely opposed second side, a first end, a second end, and a means for securing suited for attachment to a bridle or halter such that the noseband positions above the nostrils and below the eyes of a horse;
   b) first and second front panels with each having a plurality of apertures that are positioned spaced apart over the first side, and attached to the elongated band so as to form first and second vented pockets with each vented pocket having an opening and being spaced apart from the other;
   c) first and second absorbent pads comprised of compressed cellulosic fiber that are each rigid, have surface area, are sized to be slidingly and removably received into a vented pocket through the opening, have an absorbent capacity for natural oils in an amount no less than about two hundred percent (200%) of the absorbent pad's dry weight such that the natural oils are retained within the pad and such that an evaporative release of natural oils occurs at ambient temperatures, and are positioned into the first and second vented pockets; and
   d) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad wherein said oil formulation evaporates at ambient temperatures and said insert is a repellent for flies such that the time spent by flies within a one-foot radius of the absorbent pad is less than the time if there was no evaporation of natural oils.

22. A device that is an insect repellent noseband comprised of a noseband, a means for securing to a bridle or a halter, and one or more compartments of claim 2 attached to the noseband utilizing the means for securing.

23. A device that is an insect repellent brow band that is attachable to a bridle or a halter, such device being comprised of:
   a) an elongated band comprised of a high-density polyethylene that forms a first side and oppositely opposed second side, a first end, a second end, and means for securing suited for attachment to a bridle or halter such that the brow band positions above the eyes and below the ears of a horse;
   b) first and second front panels with each having a plurality of apertures that are positioned spaced apart over the first side and attached to the elongated band so as to form first and second vented pockets with each vented pocket having an opening and being spaced apart from the other;
   c) first and second absorbent pads comprised of compressed cellulosic fiber that each are rigid, have surface area, are sized to be slidingly and removably received into a vented pocket through the opening, have an absorbent capacity for natural oils in an amount no less than about two hundred percent (200%) of the absorbent pad's dry weight such that the natural oils are retained within the pad and such that an evaporative release of natural oils occurs at ambient temperatures, and are positioned into the first and second vented pockets; and
   d) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad wherein said oil formulation evaporates at ambient temperatures and said insert is a repellent for flies such that the time spent by flies within a one-foot radius of the absorbent pad is less than the time if there was no evaporation of natural oils.

24. A device that is an insect repellent brow band comprised of a brow band, a means for securing to a bridle or a halter, and one or more compartments of claim 2 attached to the noseband utilizing the means for securing.

25. A device that is an insect repellent poll band that is attachable to bridle or a halter, such device being comprised of:
   a) an elongated band comprised of high-density polyethylene that forms a first side and oppositely opposed second side, a first end, a second end, and means for securing suited for attachment to a bridle or halter such that the poll band positions behind the ears of a horse;
   b) first and second front panels with each having a plurality of apertures that are positioned spaced apart over the first side and attached to the elongated band so as to form first and second vented pockets with each vented pocket having an opening and being spaced apart from the other;
   c) first and second absorbent pads comprised of compressed cellulosic fiber that are rigid, have surface area, are sized to be slidingly and removably received into a vented pocket through the opening, have an absorbent capacity for natural oils in an amount no less than about two hundred percent (200%) of the absorbent pad's dry weight such that the natural oils are retained within the pad and such that an evaporative release of natural oils occurs at ambient temperatures, and are positioned into the first and second vented pockets; and
   d) a natural oil formulation an oil formulation comprising about 40 to about 67 percent by weight citronella oil; about 30 to about 40 percent by weight cedarwood oil and 0.00 to 30 percent by weight eucalyptus oil absorbed on said pad wherein said oil formulation evaporates at ambient temperatures and said insert is a repellent for flies such that the time spent by flies within a one-foot radius of the absorbent pad is less than the time if there was no evaporation of natural oils.

26. The repellant insert of claim 1 where said insert is inserted into a vented pocket of a a cheek band having one or more vented pockets.

27. The vented compartment of claim 2 where one or more are attached utilizing a means for securing to a cheek band.

* * * * *